United States Patent [19]

Crouch

[11] Patent Number: 4,537,034
[45] Date of Patent: Aug. 27, 1985

[54] METHOD FOR CONTROLLED REDUCTION IN TEMPERATURE AND PRESERVATION OF EMBRYOS IN A CRYOGENIC STATE

[76] Inventor: Michael D. Crouch, 9312 Highland Garden, Baton Rouge, La. 70811

[21] Appl. No.: 620,501

[22] Filed: Jun. 14, 1984

Related U.S. Application Data

[62] Division of Ser. No. 402,840, Jul. 29, 1982, Pat. No. 4,459,825.

[51] Int. Cl.³ ............................................. F25D 25/00
[52] U.S. Cl. ............................................ 62/62; 62/78
[58] Field of Search .................... 62/62, 78, 457, 404, 62/407, 440

[56] References Cited

U.S. PATENT DOCUMENTS

| | | | |
|---|---|---|---|
| 3,088,290 | 5/1963 | Zearfoss, Jr. ............................ | 62/78 |
| 3,092,974 | 6/1963 | Haumann et al. ....................... | 62/62 |
| 3,407,120 | 10/1968 | Weiss et al. ........................... | 195/104 |
| 3,717,552 | 2/1973 | Hondermarck et al. ............. | 195/142 |
| 3,795,521 | 3/1974 | Richard ................................ | 426/51 |
| 4,036,699 | 7/1977 | Quigg ................................... | 195/142 |
| 4,073,696 | 2/1978 | Müller ................................... | 195/142 |
| 4,238,337 | 12/1980 | Peters et al. ......................... | 210/179 |

Primary Examiner—Ronald C. Capossela
Attorney, Agent, or Firm—John E. Reilly

[57] ABSTRACT

An apparatus for reducing the temperature of articles to the cryogenic state in reducing the temperature of embryos at a controlled and predetermined rate is disclosed comprised of a housing defining an insulated cooling chamber employed in association with support means for removably suspending the embryos within a chamber. A gaseous medium, such as, air circulates along a closed path through the chamber so that the embryos are disposed in its path and a heat exchanger including a heat transfer medium is positioned in the flow path of the gaseous medium together with a temperature sensor so that the rate of cooling may be programmed and regulated automatically by correlation of the temperature sensor with the heat exchange medium. The method comprises the steps of removably supporting embryos in an insulated chamber; positioning a heat transfer medium therein; circulating air or another gaseous medium through the chamber across the heat transfer medium and the embryos; and programming the rate of cooling of the air by imposing close control over the temperature of the heat transfer medium while avoiding uneven temperature zones in the chamber.

4 Claims, 5 Drawing Figures

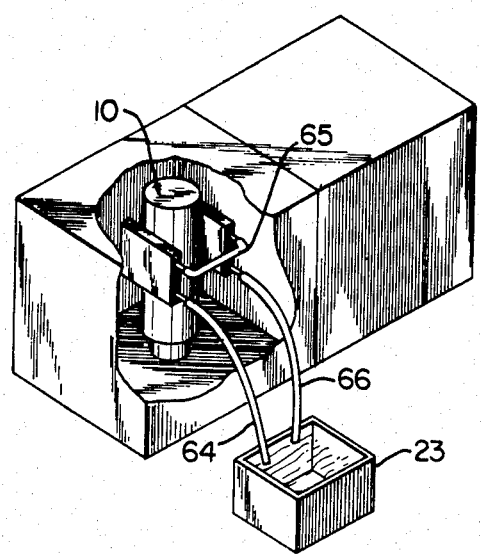
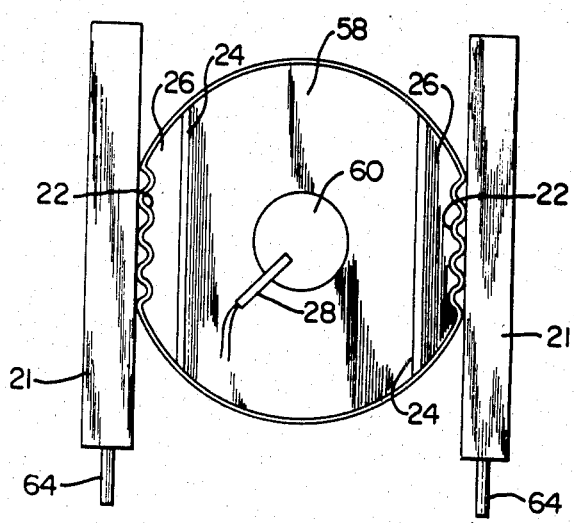
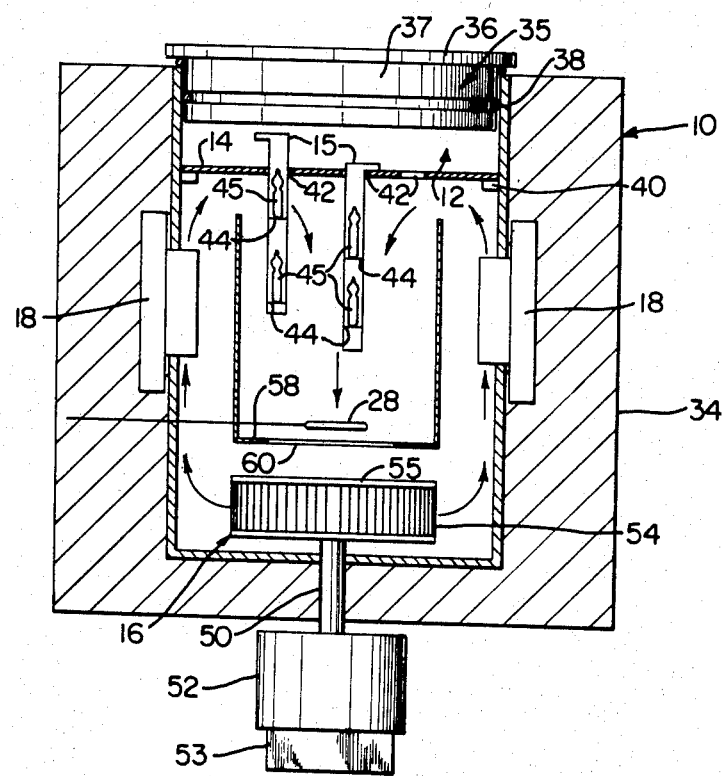

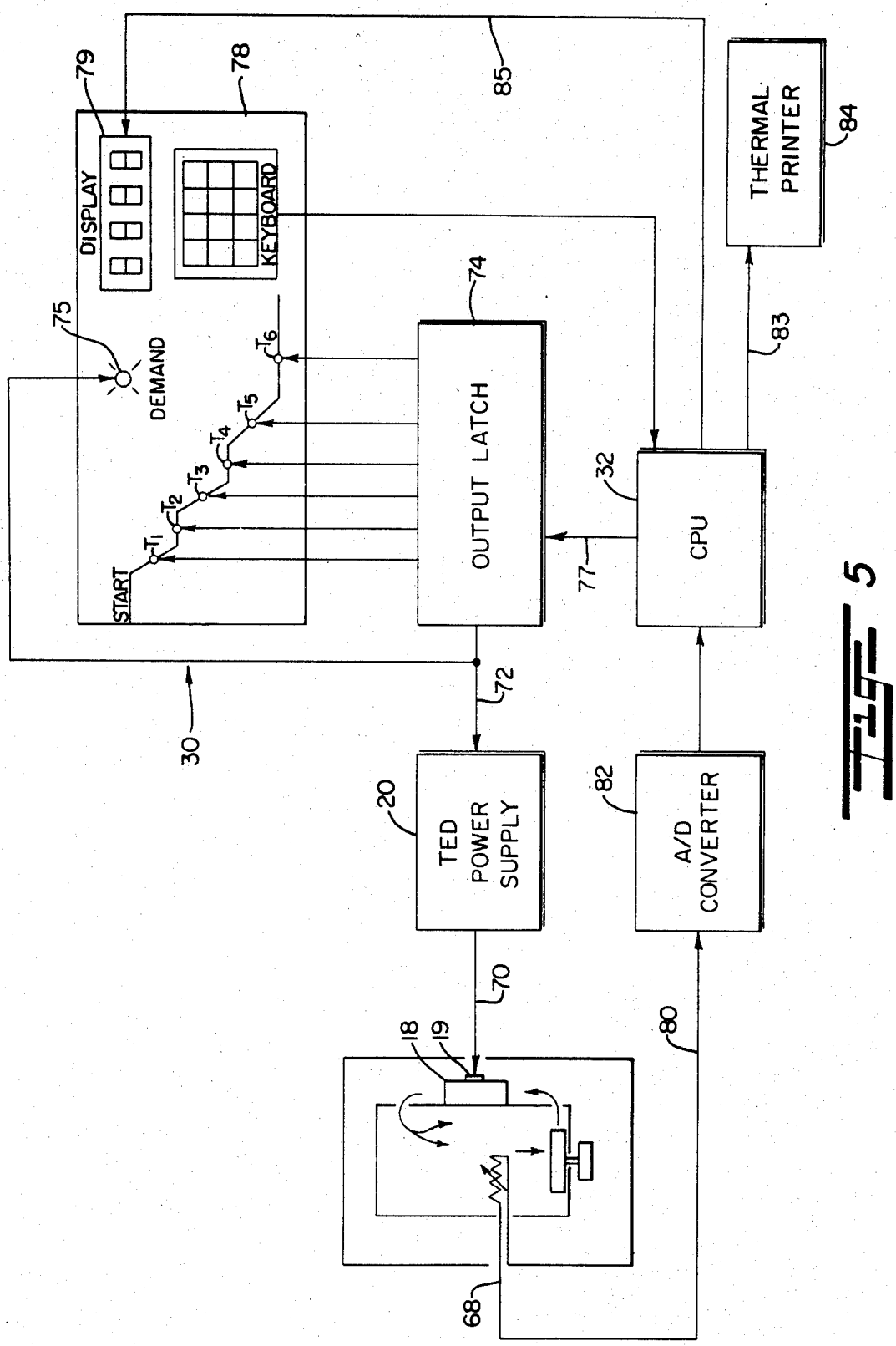

METHOD FOR CONTROLLED REDUCTION IN TEMPERATURE AND PRESERVATION OF EMBRYOS IN A CRYOGENIC STATE

This application is a divisional application of Ser. No. 402,840, filed July 29, 1982, now U.S. Pat. No. 4,459,825 for APPARATUS FOR CONTROLLED REDUCTION IN TEMPERATURE AND PRESERVATION OF EMBRYOS IN A CRYOGENIC STATE, invented by Michael D. Crouch.

This invention relates to cryogenic systems; and more particularly relates to a novel and improved method and apparatus for regulating the rate of cooling and temperature level of a wide range of articles to be maintained in a frozen or cryogenic state.

BACKGROUND AND FIELD OF INVENTION

Cryogenic systems are finding an increasing number of applications in the low temperature storage or preservation of materials; for instance, biological elements or specimens, such as, animal or human embryos, tissues and blood cells; also, the freezing point determination of products for jet fuel or semi-conductors. The method and apparatus of the present invention is directed specifically to the controlled reduction of temperature, or cooling rate, in order to place those materials in a frozen state at extremely low temperatures. In the past, it has been found to be very critical to regulate the rate of cooling or reduction in temperature of many articles, particularly embryos, tissue, blood cells and the like both in order to reduce uneven temperatures within the chamber as well as to avoid any adverse effects on the materials to be preserved or frozen. Liquid nitrogen has been in wide use in the cooling and storage of articles in a cryogenic state because of its ability to drop the temperature to extremely low levels on the order of $-35°$ C. and less. The major problem in the use of liquid nitrogen for cryogenic devices is its lack of control over chamber temperature and its cooling rate as well as the cost of purchasing and storage of liquid nitrogen. It is therefore desirable to provide a method and means of reducing the temperature of articles which will permit the use of other gaseous mediums, such as, air which can be more closely controlled than liquid nitrogen in regulating the cooling rate of the articles and at the same time obviate the use of sophisticated controls and mediums, such as, liquid nitrogen, particularly in those temperature ranges found to be most critical in avoiding any damage or permanent alteration in the molecular structure of the articles being treated.

I am not aware of the utilization of air in the controlled cooling of articles under extremely low temperature conditions, such as, in the range of 0° C. to $-35°$ C. Other apparatus has been devised which employs heat exchangers as well as temperature controllers in connection with monitoring apparatus for cell growth, depectinization of juices and fermentation systems. Representative patents in this area are U.S. Pat. Nos. 3,407,120 to R. E. Weiss et al.; 3,717,552 to J. C. Hondermarck et al.; 3,795,521 to J-P Richard; 4,036,699 to D. J. Quigg; 4,073,696 to H. Muller; and 4,238,337 to M. F. Peters et al. Nevertheless, none is directed to a cryogenic system for reducing the temperature of articles and materials, such as, encapsulated embryos, tissues or blood cells with the use of air as a gaseous medium in or through a temperature range of 0° C. to $-50°$ C. in the manner in which I have devised.

SUMMARY OF THE INVENTION

It is therefore a feature of the present invention to provide for a novel and improved method and apparatus for the controlled reduction in temperature of articles for their preservation in an extremely low temperature condition or frozen state.

Another object of the present invention is to provide for programmed control over the reduction in temperature of biological specimens in such a way that air can be employed as a gaseous medium in reducing the temperature of the articles in the temperature range of 0° C. to as low as $-50°$ C.

It is a further object of the present invention to provide for a cryogenic system which can be utilized either independently or in combination with liquid nitrogen chambers to bring about the most efficacious manner and method of controlled temperature reduction to preserve articles and their materials in their frozen state in a reliable and highly efficient manner.

Yet another object of the present invention is to provide in a cryogenic system for preserving embryos and the like for a novel and improved programmed control over the rate of cooling and which is readily conformable for use in the treatment of a wide range of articles.

It is an additional object of the present invention to provide a cryogenic system for cooling articles to extremely low temperatures having a novel and improved chamber for removable suspension of the articles, the circulation of a gaseous medium with respect to the articles as well as the controlled reduction in temperature of the gaseous medium in such a way as to maintain close, accurate control over the actual rate of temperature drop of the articles themselves.

In accordance with the present invention, there has been devised a novel and improved method and apparatus for reducing the temperature of articles to the cryogenic state. Without limiting the breadth of application of the method and apparatus of the present invention, it may be best typified by describing its use in reducing the temperature of cattle embryos at a controlled and predetermined rate. In the apparatus of the present invention, a housing defining an insulated cooling chamber is employed in association with support means for removably suspending the embryos within said chamber. Gaseous medium circulating means are operative to circulate a gaseous medium along a closed path through the chamber such that the embryos are disposed in the path of circulation of the gaseous medium, and heat exchange means including a heat transfer medium is positioned in the path of flow of the gaseous medium together with a temperature sensor so that the rate of cooling may be programmed and regulated automatically by correlation of the temperature sensing means with the heat exchange medium. In the preferred form, air is employed as the gaseous medium and is circulated by means of a blower to follow a path of flow around the inner walls of the chamber, against the support means which holds the embryos in place, then is reversed in direction to pass centrally of the chamber back into the suction side of the blower. Extremely close, programmed control over the cooling rate is established by regulating the voltage applied to a reverse thermocouple forming a part of the heat exchange means which has the heat transfer medium intruding into the chamber adjacent to the chamber walls so as to be in the path of flow of the air from the blower, and the temperature sensor is located in the path of flow of air past the embryos preliminary to its return into the suction side of the blower.

In the method of the present invention the following steps are employed: removably supporting embryos in an insulated chamber; positioning a heat transfer medium in said chamber; circulating air or another gaseous medium through said chamber across said heat transfer medium and said embryos; and programming the rate of cooling of said gaseous medium by imposing a close control over the temperature of said heat transfer medium whereby the cooling rate is controlled on the order of 1° per minute in the range of −2° C. to −22° C. while avoiding uneven temperature zones in the chamber.

The above and other objects, advantages and features of the present invention will become more readily understood and appreciated from a consideration of the following detailed description of a preferred embodiment when taken together with the accompanying drawings in which:

BRIEF DESCRIPTION OF THE DRAWINGS

FIG. 2 is a plan view illustrating in more detail the interrelationship between the heat exchange means and cryogenic chamber;

FIG. 3 is a cross-sectional view illustrating in more detail the path of air flow through the chamber;

FIG. 4 is a somewhat schematic view of the heat exchange means employed in association with the present invention; and FIG. 5 is a flow diagram illustrating the programmed temperature controller employed in association with the cryogenic chamber of the present invention.

DETAILED DESCRIPTION OF THE PREFERRED EMBODIMENT

Figure 1:
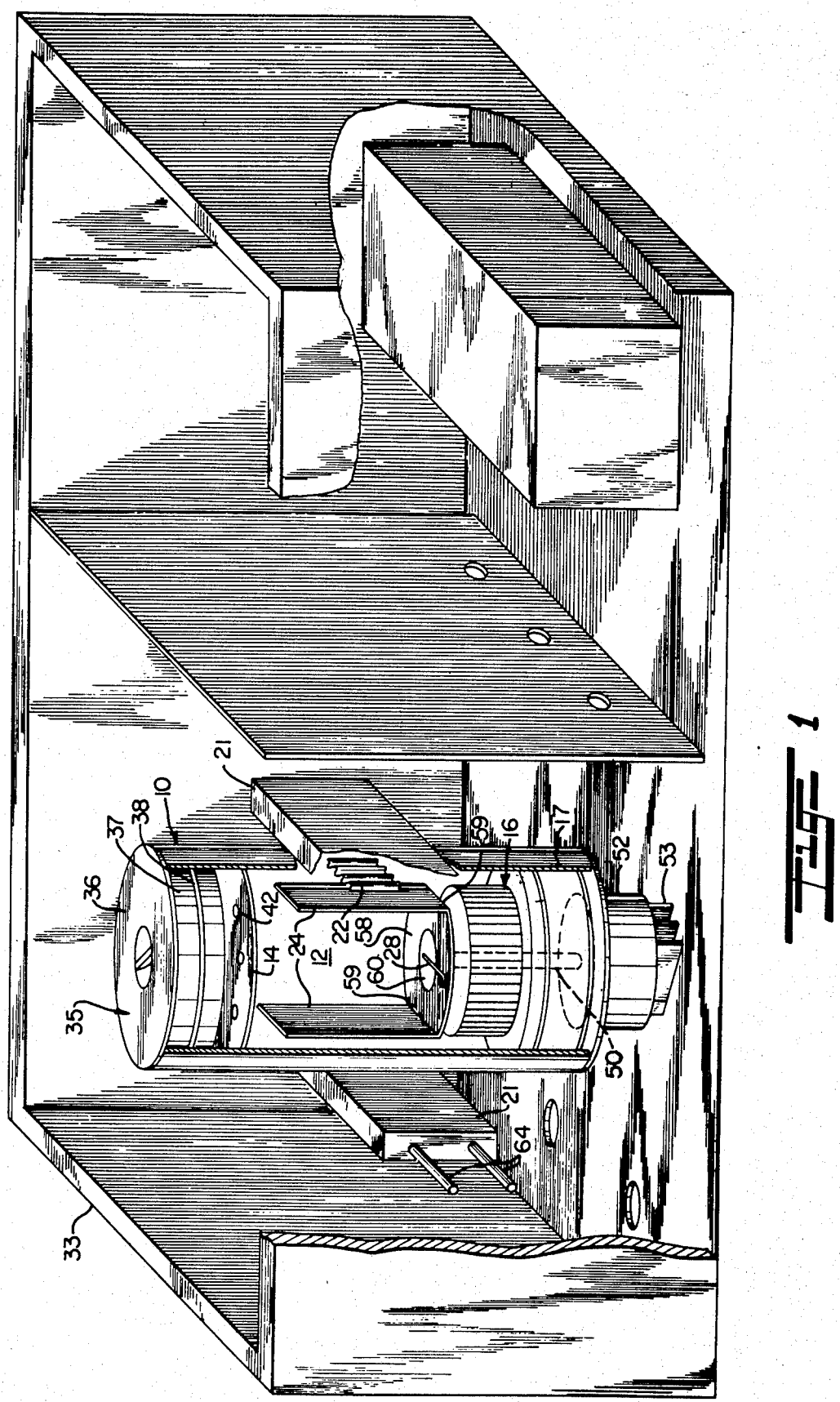
FIG. 1 is a perspective view of a preferred form of cryogenic chamber and programmed controller means in accordance with the present invention.

Referring in more detail to the drawings, a preferred form of cryogenic system in accordance with the present invention broadly comprises a housing 10 which defines an insulated cooling chamber 12. A removable support member 14 is insertable into one end of the chamber 12 and includes a plurality of embryo support canes 15 of conventional construction. A gaseous medium, preferably air, is circulated in a closed path through the chamber 12 by a blower or fan 16 which is mounted in the base 17 of the chamber, i.e. in the opposite end of the chamber to that of the support member 14. Generally, the blower will maintain a path of circulation axially along the chamber wall against the upper support 14 then is reversed and caused to flow downwardly along the central area of the chamber across the encapsulated embryos. Heat exchangers 18 are in the form of thermoelectric devices, each including a reverse thermocouple 19 to which voltage is applied by a power source 20, and a heat transfer medium in the form of convoluted fins 22 intrude into a diametrically opposed wall portions of the chamber 12 from communication with a heat exchanger or plenum 21, the fins 22 being disposed directly in the path of the air flow from the fan 16.

As illustrated in more detail in FIGS. 2 to 4, inclusive, the heat exchanger contains a suitable coolant, such as, water which is circulated into the plenums or heat sinks 21 in heat exchange relation to the fins 22 from a supply tank 23. Baffle plates 24 extend longitudinally of the chamber in spaced relation inwardly of the heat transfer fins 22 and terminate just short of the upper end or support member 14 to aid in regulating air circulation through the outside areas 26 which are formed between the baffle plates 24 and chamber 12 so as to pass in direct heat transfer relation to the fins 22. In order to regulate the cooling rate, a temperature sensor 28 is disposed in the return path of air flow and is electrically connected into an electric control circuit 30 shown in FIG. 5. The circuit 30 includes a microprocessor represented at 32 in a closed feedback loop which in response to the rate of temperature reduction will operate through the power source 20 to regulate the amount of voltage applied to the reverse thermocouple 19 in a manner to be hereinafter described.

In the preferred form, the housing 10 is positioned in upright relation within an outside enclosure represented at 33. The housing 10 is of generally cylindrical configuration having an insulated outer wall 34 which may suitably be composed of a polyurethane foam insulation material, the upper end normally enclosed by an insulated cover 35 of generally circular configuration. The cover has an outer rim 36 overlapping the upper end of the cylindrical outer wall 34 and a central body 37 which projects into the chamber for a limited distance and is provided with one or more annular sealing rings 38 dimensioned to sealingly engage the inner surface of the wall 34. Spaced inwardly of the body 37 within the chamber is a radially inwardly directed rib 40 upon which the intermediate support plate 14 is seated. The plate 14 is of circular configuration and has a plurality of spaced openings 42 which are sized for close-fitting insertion of the canes 15. In a well-known manner, the canes 15 may be of the type formed of open or slotted tubes having ledges 44 at longitudinally spaced intervals. The embryos are encapsulated in a well-known manner within vials 45 and are positioned on each ledge 44 so as to be directly exposed to the return air flowing thereacross.

The fan 16 is preferably a squirrel cage fan, as shown, which is supported for rotation in the base of the chamber on an upwardly directed drive shaft 50 of motor 52 which is disposed externally of and beneath the chamber 12. The shaft 50 extends upwardly through the insulated base, and the motor 52 is positioned on a heat sink which may be in the form of aluminum fins 53 so as to minimize heating of the motor or its shaft which could otherwise be transmitted into the interior of the chamber 12. The fan is so constructed as to discharge the air in an outward radial direction through its outer periphery 54 and having an upper return at its central inlet or suction side 55.

In order to assist in constraining the flow of air upwardly along the heat transfer fins 22, the baffle plates 24 are preferably mounted on an annular support plate or base 58 which is sized to correspond to the diameter of the chamber except at diametrically opposed flatted edges 59 where the baffle plates 24 are caused to extend upwardly in diametrically opposed relation to one another and thus form clearance spaces or areas 26 in diametrically opposed relation for upward movement of the air from the fan. The temperature sensor 28 is suspended on the base 58 to project into the hollow central opening 60 in the base and to be in the path of flow of air which is returned along the center of the chamber into the inlet 55.

As shown in detail in FIGS. 2 to 4, the preferred form of thermoelectric device includes the fins 22 in the form of convoluted aluminum fins which are attached to the inner wall surfaces of each of the plenums 21 which surround the thermocouple assemblies 19 of the thermoelectric devices 18, the inner surfaces of the air fins defining diametrically opposed wall surfaces of the chamber 12 with their convolutions extending parallel to the direction of air flow. A source of coolant or water supply represented at 23 includes conduits 64 extending from the supply to one plenum or heat sink 21, an intermediate conduit 65 interconnecting the heat sinks 21 to conduct the coolant from the first to the second heat sink 21, and a return line or conduit 66 extending from the second heat sink 21 back to the coolant supply source. Here, the heat sinks are of generally elongated rectangular configuration and each contains a thermocouple assembly 19 which as described is preferably of the reverse thermocouple type. One such assembly is the Model 806-1008-01 thermoelectric assembly manufactured and sold by Cambion of Cambridge, Mass. and which is a two-stage device having a 31/186 couple ratio capable of operating over a temperature range of $-55°$ C. to $+125°$ C. Each heat sink or plenum 21 is a liquid cooled exchanger used to remove waste heat from the thermoelectric component, and ordinary tap water may be used as the cooling fluid. The temperature sensor may be a resistance thermometer, also available from Cambion of Cambridge, Mass. and has suitable leads 68 which extend into the control circuit as illustrated in FIG. 5.

The operation of the cryogenic system of the present invention may be best described in relation to the electrical control circuit as shown in FIG. 5 in regulating the cooling rate of the chamber. As schematically illustrated in FIG. 5, in the electrical control circuit 30 the power supply 20 directs an output signal over line 70 to the thermoelectric devices 18, there being one device illustrated in FIG. 5. The power supply is regulated by a demand signal applied over line 72 from output latch circuit 74. In that the thermoelectric devices employ reverse thermocouples as described, the greater the rate of cooling required, the more or increased voltages applied to the reverse thermocouples 19. In this connection, the cooling rate is preselected and programmed into microprocessor 32 which applies control signals to the output latch circuit 74 through the display panel 78. The display panel includes display lights as represented at 79 to numerically indicate various parameters or working conditions in the cryogenic chamber, such as, the rate of cooling, temperature level at any given point in time, etc. A typical cooling rate to be programmed into the microprocessor is represented on the display panel 78 and indicates various temperature levels over given periods of time to be reached by the cryogenic chamber. For instance, this temperature range may extend from a starting point of 40° down to $-35°$ C. or lower. Also programmed into the microprocessor is the desired cooling rate as designated at $T_1$ through $T_6$ between each temperature level including dwell periods where, for example, it is desirable to maintain the temperature at a constant level over a limited period of time followed by a rapid reduction to a next temperature level. The temperature level sensed in the chamber 12 by sensor 28 is applied as an analog signal over line 80 to an analog-to-digital converter 82 which conditions and converts the analog signals into digital pulses to be applied to the microprocessor 76. The microprocessor in turn compares those signals with the programmed temperature level and directs correction signal over line 77 to the latch circuit 74. The signals are also directed over line 83 to a thermal printer 84 and over line 85 to LED display 79. Thus, at any given instant of time if the temperature sensed in the chamber departs from the preselected temperature level programmed into the microprocessor 32, the microprocessor 32 will generate a correction signal either to increase or reduce the applied power to the thermocouples 19.

Of particular importance in controlling the cooling rate for the treatment and preservation of materials, such as, embryos is to avoid sudden reductions in temperature as the embryos pass through the freezing point and continue into the range of 0° C. to $-22°$ C. By the utilization of a gaseous medium, such as, air the cooling rate can be more closely regulated and at the same time reach the extremely low temperatures required for proper preservation of the embryos. As represented by the temperature curve on the display panel, the reverse thermocouples 19 are capable of undergoing variable cooling rates through different temperature ranges and be periodically interrupted by dwell periods or constant temperatures for predetermined time periods.

For the purpose of illustration and not limitation, on the display panel $T_1$ may represent a drop in temperature from 40° C. to 20° C. at $T_2$. The temperature is then held for a controlled time interval, such as, on the order of five minutes. In the period $T_3$, the temperature is dropped at the rate of 1° C. per minute to $-7°$ C., and is held at that level for another controlled period, such as, five minutes as designated at $T_4$. At $T_5$ the temperature is dropped at the rate of $-3°$ C. per minute to $-30°$ C. as represented at $T_6$. Throughout the cooling cycle, the temperature is constantly monitored both with respect to temperature level and cooling rate to be sure that it follows the programmed rate of cooling. Thus, at any point if the temperature level or rate of cooling varies from that program, a correction signal is applied either to reduce or increase the applied voltage. For instance, if the temperature should be above the program level, the voltage is increased and if it should be below the program level the voltage is reduced by virtue of the specific reverse thermocouple arrangement employed. Correspondingly, if the cooling rate should be less than that programmed, the voltage is increased, and the reverse is true if the cooling or temperature drop rate is greater than that to program. Again, the particular temperature curve illustrated is only one typical program and virtually any temperature curve may be substituted depending upon the articles being frozen and reduced to extremely low temperature conditions. Very often in the case of embryos it is desirable to utilize the cryogenic chamber of the present invention to reduce the embryos to a temperature level as low as $-50°$ C., followed by removal of the embryos from the chamber and placement in a nitrogen chamber which is capable of reducing their temperature still further. To this end, all that is necessary is to remove the outer cover 35 followed by removal of the intermediate lid 14 and suspended embryos. Then, if desired, a new batch of embryos may be suspended in the lid and replaced in the chamber. During the replacement interval, it is customary practice to maintain the fan 16 in operation as well as the thermoelectric devices 18 so that the next batch of embryos will undergo immediate preliminary cooling as soon as they are placed in the chamber and the outer cover is repositioned.

The demand light 75 on the display panel provides a visual indication of the amount of voltage applied to the thermoelectric devices. As the voltage level increases, the demand light intensity will increase. In this way, there may be situations where the operator will want to modify the program to reduce the amount of voltage supply, or vice versa, depending upon the particular conditions of the chamber as indicated by the LED display 79. The thermal printer 84 operates in a well-known manner to provide a hard copy or printed record of the temperature program selected and the actual performance of the cryogenic device during a run or cycle. For example, a typical printout would include time in minutes, programmed temperature at that point in time and actual temperature. In turn, a keyboard 86 will permit a variety of temperature programs to be entered by the operator in accordance with the application desired, such as, freezing of animal embryos, human liver tissue, etc. The keyboard may be numeric or alphanumeric to permit entry of the desired program in regulating the rate of reduction of temperature throughout a given cycle. It is also desirable to permit monitoring of the amperage or current level for the power supplies 20 for optimum performance and cooling capacity, since the amperage will change in the thermoelectric devices by the changes in temperature. The fan 16 most desirably is capable of operating in the range of 3,000 rpm with an output or air flow approximating 100 cubic feet per minute when used in cattle embryo freezing systems where the chamber 12 is given a diameter on the order of 4" and a length or height on the order of 12" between the base 58 and the movable support plate 14.

It is therefore to be understood that various modifications and changes in the construction and arrangement of parts and sequence of steps employed in the preferred form of invention may be made without departing from the spirit and scope of the present invention as defined by the appended claims.

I claim:

1. The method of freezing embryos at a controlled rate from room temperature to cryogenic temperatures on the order of $-50°$ C. comprising the steps of:
   providing an insulated, sealed chamber in which said embryos are removably supported;
   positioning a heat transfer medium in said chamber;
   recirculating air under pressure through said chamber along a closed path into direct contact with said heat transfer medium followed by passing said air across said embryos to progressively reduce the temperature in said chamber to a cryogenic temperature on the order of $-50°$ C.; and
   programming the rate of cooling of said air by regulating the temperature of said heat transfer medium.

2. The method according to claim 1, wherein the air is caused to flow in an axial direction first along the inner wall surfaces of said chamber and to return along the central axis of said chamber.

3. The method according to claim 2, including the step of removably positioning said embryos in one end of said chamber and directing the air into the opposite end of said chamber whereby to cause it to undergo a reversal in direction at the one end of said chamber.

4. The method according to claim 1, including the step of incrementally reducing the temperature of the embryos at a rate on the order of 1° C. to 3° C. per minute in the temperature range between 0° C. and $-35°$ C.

* * * * *